United States Patent
Czaja et al.

(10) Patent No.: US 9,600,635 B2
(45) Date of Patent: *Mar. 21, 2017

(54) MEDICATION DISPENSING SYSTEM

(71) Applicant: Anelto, Inc., The Colony, TX (US)

(72) Inventors: Stanislaw Czaja, Cardiff, CA (US); Muhammad Afsar, San Diego, CA (US); Ilona Stawski, Avon Lake, OH (US)

(73) Assignee: ANELTO, The Colony, TX (US)

( * ) Notice: Subject to any disclaimer, the term of this patent is extended or adjusted under 35 U.S.C. 154(b) by 70 days.

This patent is subject to a terminal disclaimer.

(21) Appl. No.: 14/222,643

(22) Filed: Mar. 23, 2014

(65) Prior Publication Data

US 2014/0207278 A1    Jul. 24, 2014

Related U.S. Application Data

(63) Continuation-in-part of application No. 12/853,511, filed on Sep. 13, 2010, now Pat. No. 8,725,291.

(51) Int. Cl.
   *G06F 19/00* (2011.01)
(52) U.S. Cl.
   CPC ...... *G06F 19/3462* (2013.01); *G06F 19/3456* (2013.01)

(58) Field of Classification Search
   USPC ........................ 700/237, 240, 244
   See application file for complete search history.

(56) References Cited

U.S. PATENT DOCUMENTS

| | | | |
|---|---|---|---|
| 7,885,725 B2 * | 2/2011 | Dunn ................. | G06F 19/3462 700/236 |
| 8,108,068 B1 * | 1/2012 | Boucher ............. | A61J 7/0084 700/236 |
| 8,725,291 B2 * | 5/2014 | Czaja ................. | G06F 19/3456 700/237 |
| 2009/0315702 A1 * | 12/2009 | Cohen Alloro ....... | A61J 7/0409 700/225 |

* cited by examiner

*Primary Examiner* — Timothy Waggoner
(74) *Attorney, Agent, or Firm* — Andrews Kurth Kenyon LLP; Sean S. Wooden

(57) ABSTRACT

Medication dispensing system for remote monitoring of the daily dispensing of medication and pre/post dispense monitoring of medication effected physiological functions is disclosed. In one embodiment a dispensing unit equipped with weight sensing mechanism such as scale or balance communicates with a monitoring application residing in a wireless terminal. The monitoring application provides supervision over a medication dispensing process.

7 Claims, 8 Drawing Sheets

MEDICATION DISPENSING SYSTEM

RELATED U.S. APPLICATION

This application is Continuation in Part of non-provisional application Ser. No. 12/853,511 titled "Method and Apparatus for Remote Monitoring of Dailey Dispensing of Medication" filed on Sep. 13, 2010.

FIELD OF THE INVENTION

The present invention relates to the field of wireless health Monitoring system, specifically to the monitoring of daily dispensing of medications.

DESCRIPTION OF THE RELATED ART

As the national health care systems cope with the increasing the cost of care for the growing number of patients with chronic diseases, or an elderly requiring a daily dose of medication to sustain their quality of life, there is a need for a low cost, low maintenance monitoring system that insures that the patient actually remembers to take his/her daily dose of medication at the correct time.

In recent years, the use of mobile devices and, in particular, cellular telephones has proliferated. As a result, cellular telephones or other wireless devices, installed in primary residences, are considered as candidates to provide various health care-monitoring and even health care-delivering functions.

Considering that strict adherence to the timely dispensing of medication is critical to the quality of provided health care, combining of simple dispensing mechanism with the ubiquitous cellular phone can provide the benefits of virtual medical supervision of the medication dispensing regime at very low cost.

Many medication dispensing methods were proposed in the past—from very simple containers with daily compartments and a textual information cards, through programmable dispensing systems, to complex systems intended for centralized dispensing in hospitals. However, none of these systems provides a quality of medical supervision at costs applicable for personal use.

Most dispensing systems intended for a personal use consist of a daily, weekly, etc. containers and textual information card describing dosage to be dispensed at each dispensing period. Sometimes the supplied information card allows the patient to enter "reminder" information. While previous devices provide some form of organized dispensing for personal use, they lack the ability to verify usage and/or to allow intervention should usage not occur or be inaccurate.

Another type of a medicine dispensing system intended for a personal use consists of a programmable device capable of time-tracking and reminding the patient when to take their next medication. Such devices provide some enforcement of medication regime, but their capability is limited to a simple audio or visual reminder and unable to verify medication compliance or receive instructions from a remote medical supervisor.

Another type of medicine dispensing system embeds some supervisory function either in the medication packaging, or rely on complicated electromechanical system where each type of the medication (pill) resides in a separate container with the dispensing from those multiple containers controlled by the micro-processor, or an electromechanical pill dispenser. A common problem of these systems is their reliance on new packaging technology (e.g. inclusion of RFID into every package, while providing no solution for multi-pill containers), or proposing complicated electromechanical dispensers unable to hold different size(s) of the medication. Moreover, none of these devices provide feedback or other important information to the medical supervisor regarding patient compliance of medication consumption.

SUMMARY OF THE INVENTION

This invention allows for the remote monitoring of the daily dispensing of prescription drugs by at-home care, an elderly patient or a clinical trial patient. The system consists of a dispensing unit equipped with sensor(s), a monitoring application and a wireless terminal, such as a cell-phone providing access to the Internet. The monitoring application and wireless Wide Area Network (WAN) modem can reside within the dispensing unit or alternatively, the dispensing unit can communicate with the application residing in the user/patient cell phone over suitable RF interface, such as Bluetooth, etc.

The proposed invention integrates a simple medication dispensing container similar to one well known from prior art with a sensitive weighting mechanism in the form of a scale or balance, or Microelectromechanical System (MEMS) sensor(s) interfacing over a short range wireless link similar to Bluetooth with the medicine dispensing application residing in the patient's cell phone.

Such a system can provide real-time monitoring of medication compliance by alerting the user when the next set of medication should be taken. In addition the dispenser can sense the removal of the medication via weight change and thereby help to confirm compliance of the dispersion of the medication. Furthermore, if the medication is not dispensed at the prescribed time, such a system may provide a local alert to the patient; remote alerts are sent to a list of patient's medical supervisors (family, friends, physicians, etc) due to non-compliance medication schedule and or dosage.

Furthermore, if such system is equipped with additional monitoring sensors such as: heart rate, blood pressure, glucose level, etc, it can provide close-loop monitoring of the patient's response to the drug delivery, thereby allowing a physician to change the medication when a negative response (or no response) to the prescribed drug has been detected. Beside compliance verification, the cell-phone based application guarantees a continuous and secure connection with clinical and family supervisors, thereby providing low cost and reliable patient care.

Such a monitoring system can operate using any of wireless WAN technology such as: cdma2000 (1×RTT and EV-DO), UMTS, LTE, WiMax, etc.

Various embodiments for a method for monitoring the daily dispensing of medication are presented.

In one embodiment, the method may include a daily medication container integrated with a scale or balance which is capable of measuring the weight of dispensed medication and an integrated wireless Persona Area Network (PAN) such as Bluetooth which interfaces with the monitoring application residing in the patient's cellular phone.

In some embodiments, the daily medication container is a separate container of any sort which can be placed on a scale or balance which is capable of measuring weight of dispensed medication integrated with PAN wireless network such as Bluetooth which interfaces with the monitoring application residing in the patient's cellular phone. In such embodiment the cell phone based application must be able to calibrate weight (and subsequent changes over time) of the medication container.

In another embodiment, the daily medication container is equipped with MEMS sensors capable of detecting the dispensing of the medication either by measuring the change of the weight, before and after dispensing, and communicate over the integrated PAN wireless network such as Bluetooth with the monitoring application residing in the patient's cellular phone.

In all of these embodiments, the monitoring application performs all the functions related to patient and medical supervisor authentication, calibration of medication containers and medication, supervision of dispensing time and medication quantity including alerts and notification to the user/patient, "book-keeping" of the dispense medication, scheduling of the next dispensing time, and in case of detected non-conformance to the prescribed dispensing regime executes local and remote alarms to other interested third parties.

Furthermore, when the application is augmented with additional sensors capable of monitoring specific bio-functions such as: pulse, heart rate, arrhythmia, blood pressure, etc. monitors, the proposed method may provide near-real-time feedback about the effects of the medication to the supervising medical professional.

BRIEF DESCRIPTION OF THE DRAWINGS

A better understanding of the present invention can be obtained when the following detailed description of the preferred embodiment is considered in conjunction with the following drawings, in which.

Figure 1:
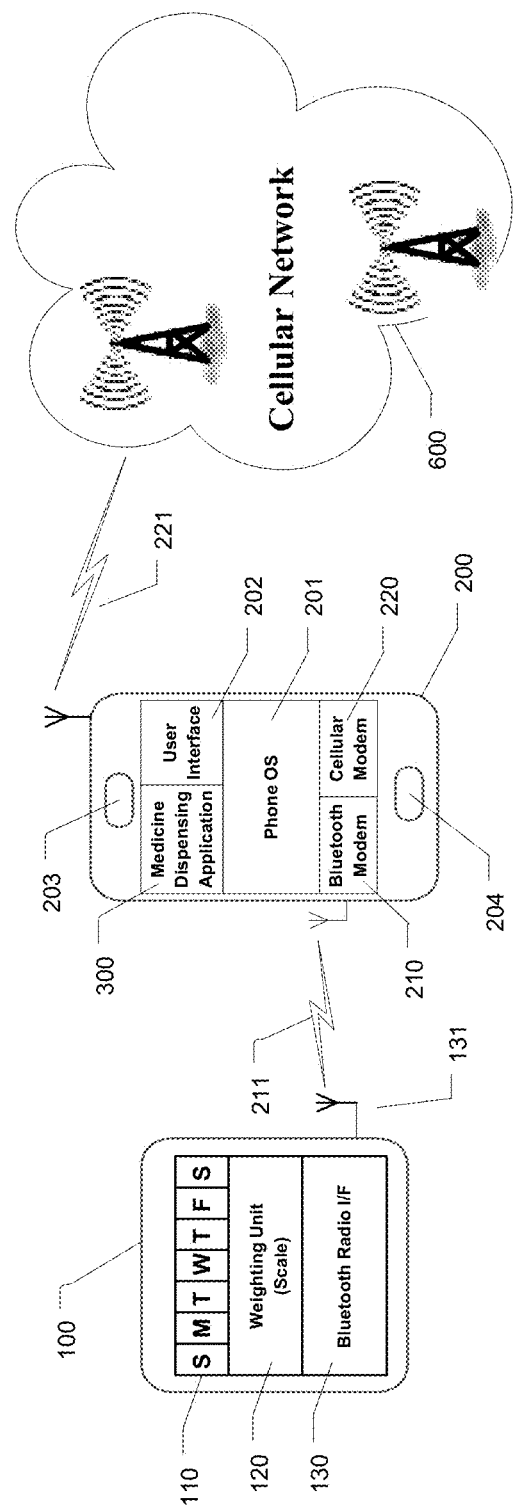
FIG. 1 is an exemplary medicine dispensing compliance system according to one embodiment.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Memory Medium—Any of various types of memory devices or storage devices. The term "memory medium" is intended to include an installation medium, e.g., a CD-ROM, floppy disks or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor, which connects to the first processor over a network, such as wireless PAN or WAN network or the Internet. In the latter instance, the second processor may provide program instructions to the first processor for execution. The term "memory medium" may include two or more memory mediums, which may reside in different locations, e.g., in different processors that are connected over a network.

Application—the term "application" is intended to have the full breadth of its ordinary meaning. The term "application" includes: 1) a software program which may be stored in a memory and is executable by a processor; or 2) a hardware configuration program useable for configuring a programmable hardware element.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Computer System—any of various types of computing or processing systems, including cell phone, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Dispense Period—in the context of this invention the period between the 1$^{st}$ day and the last day of scheduled dispensing. In this context the period may consist of several consecutive days or a period when dispense is scheduled every other day, etc.

Dispense Cycle—in the context of this invention it is the

Medical Supervisor—in the context of this invention, any person or institution (pharmacy, medical personnel, family member, etc.) authorized to enter or modify dispensing operational parameters, receive remote alerts, notifications or transmission of monitored data.

Patient—in the context of this invention, person supervised by the medicine dispensing application.

Medication Schedule—in the context of this invention, information pertaining to timing and dosage of medications, medication related instruction and other information provided to the patient by the pharmacy, or physician.

Medication Specific Instructions—in the context of this invention any instructions embedded in the schedule 2D bar-code, presented to the user at the specified time. Such time may or may not coincide with the time of medication dispense.

Pharmacy Messages—in the context of this invention, instructions and messages referenced by the message ID and inserted to the schedule 2D bar-code by pharmacy personnel. Such messages may contain: medication refill request, information about medication cross-dependencies, promotions, etc.

Provider Messages—in the context of this invention, instructions from the health provider to perform specific actions in relation to the dispense of prescribed medication, for example: conform positive/negative reaction to medication; request for pre/post dispense monitoring of certain bio-function (heart rate, glucose level, etc.), schedule office visit, etc.

Message ID—in the context of this invention a numerical identifier of a precoded message stored in the medicine dispense system memory which allows for large number of long messages to be referenced within the capacity constraint of 2D bar-code.

Precoded Message—in the context of this invention, any message referenced by the massage ID and intended for presentation to the terminal UI.

Medication Gross Weight—in the context of this invention it is the weight of the total medication pill including the active ingredients plus any additional bounding or coating compounds.

Medication Net Weight—in the context of this invention it is the weight of the medication active ingredient as listed on the medication prescription or medication capsule.

Medication Calibrated Weight—in the context of this invention it is the total weight of gross weight all medications scheduled for dispense during the current dispensing cycle plus the tar weight of the medication container.

Tar Weight—in the context of this invention it is the weight of the medication dispense container.

Medication Calibration—in the context of this invention a process by which the actual gross-weigh of the medication including the active ingredient(s), bounding and additive compounds and/or medication capsule is obtained.

Medication NDC—in context of this invention, the name of the medication reference in the FDA National Drag Code registry.

DESCRIPTION OF PREFERRED EMBODIMENT

The proposed method leverages on the properties of wireless Personal Area Network (PAN) such as Bluetooth and wireless Wide Area Network (WAN), such as a cell-phone, and combines the inherent benefits provided by those networks with the medicine dispensing device which may take the form of a simple multi-compartment container, where the compartment are labeled with the day-of-the-week and a weighting station, capable of detecting when the medications are removed and able to communicate with the cell-phone based monitoring application over short range wireless link similar to Bluetooth Assuming that both the tar weight of the dispensing container and the gross weight of a single medication is known, and the total number of individual doses in the container is known, one can determine if a single dosage of medication was dispensed by measuring the total weight of the dispense container, including medication, before and after each dispense. Such parameters may be obtained by the calibration process which will record the tar weight of the dispense container and the gross weight of single medication, then multiply such medication gross weight by the number of medication to be dispensed and adding the tar weight of the dispense container.

Such dispenser and associated weighting device is equipped with a PAN wireless communication link, such as Bluetooth. The device is controlled over this said PAN communication link by the Dispensing Application control software residing in the cell-phone which in turn is connected to the wireless WAN and consequently to the Internet. In this fashion one may provide a reliable remote medication dispense monitoring system.

In such a system the intelligence and supervision is embedded in the medication dispensing application software residing in the user/patient cell-phone. Such application determines time and dosage to be dispensed, alerts the user/patient about the dispense time, medication dosage, and verifies the correct amount of medication dispensed, and alerts the user of any discrepancy between the prescribed and dispensed dosage. In the absence of corrective action, or satisfactory explanation by the user after discrepancy, system sends an alert to the remote "medical supervisors" or other interested parties informing of medication non-compliance.

Figure 2:
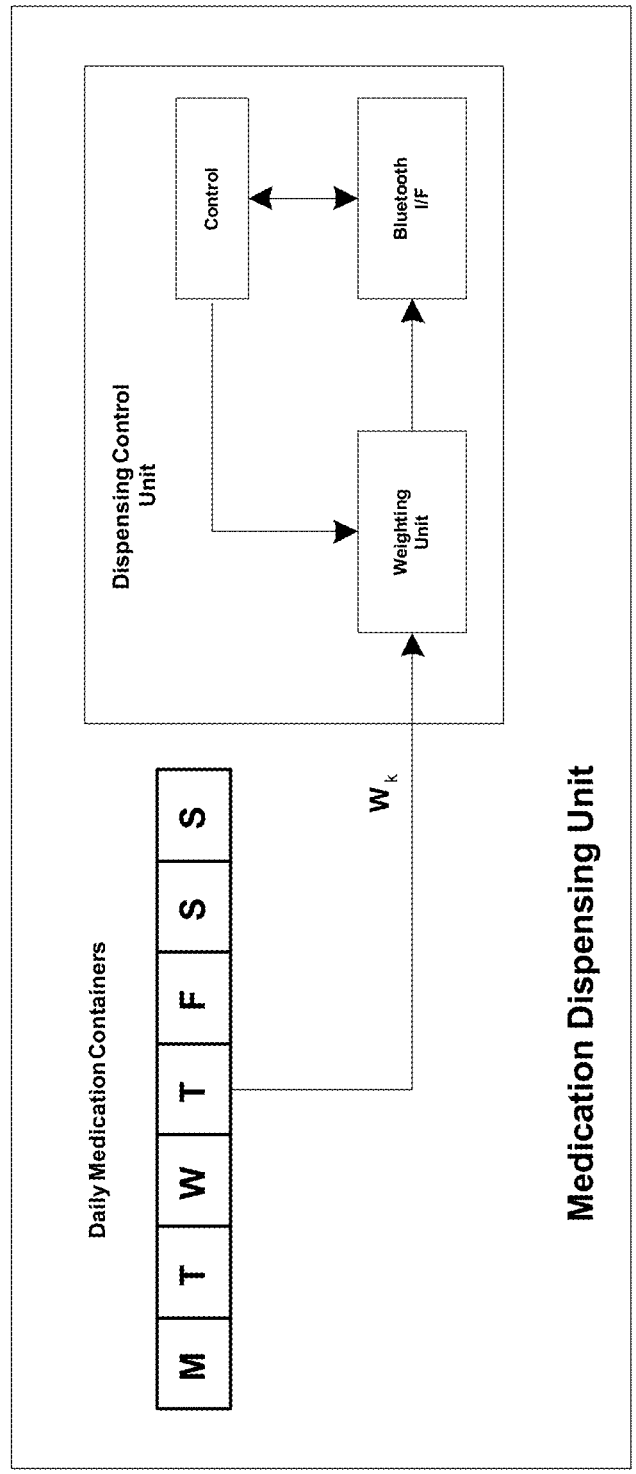
FIG. 2 is an exemplary block diagram of the medicine dispensing unit.

This invention integrates wireless access technology with a simple dispensing unit to provide reliable remote medication compliance system without requiring physical presence of health professional or family member. An example of such system is presented in FIG. 1 and FIG. 2.

The medicine dispensing unit 100 consisting of medication container 110, where each compartment is dedicated for a single day (dosage) of the medications, a weighting unit 120 capable of measuring the weight of the dispensed medication, a dispense unit control program 130 in form of stand-alone software or integrated into radio interface Media Access layer (MAC) functionality, and a PAN wireless interface 140 in form of Bluetooth, etc. communicating over the 211 RF link with the application.

The medicine dispensing application 300 resides inside the wireless phone 200, program memory and is under general control of phone Operating System (OS) 201 and communicates with the dispensing unit 100 over the phone Bluetooth radio interface 210 and with the wireless WAN network over the cellular radio interface 220 and RF link 221. Furthermore, the medicine dispensing application interfaces with the user through the phone User Interface (UI) 202, speaker 203 and microphone 204.

The wireless phone (also referred to as access terminals) 200 may include any type of device, which may be used in a cellular network, e.g., RF communication. Mobile devices 200 may include cellular (or cell) phones smart phones, personal digital assistants (PDAs) with mobile communication capabilities, laptops or computer systems with mobile communication components, and/or any device, which is operable to communicate with a cellular network. The mobile devices may use various different protocols, e.g., cdma2000 (1×RTT and EV-DO), UMTS, LTE, WiMax, or others).

Figure 3:
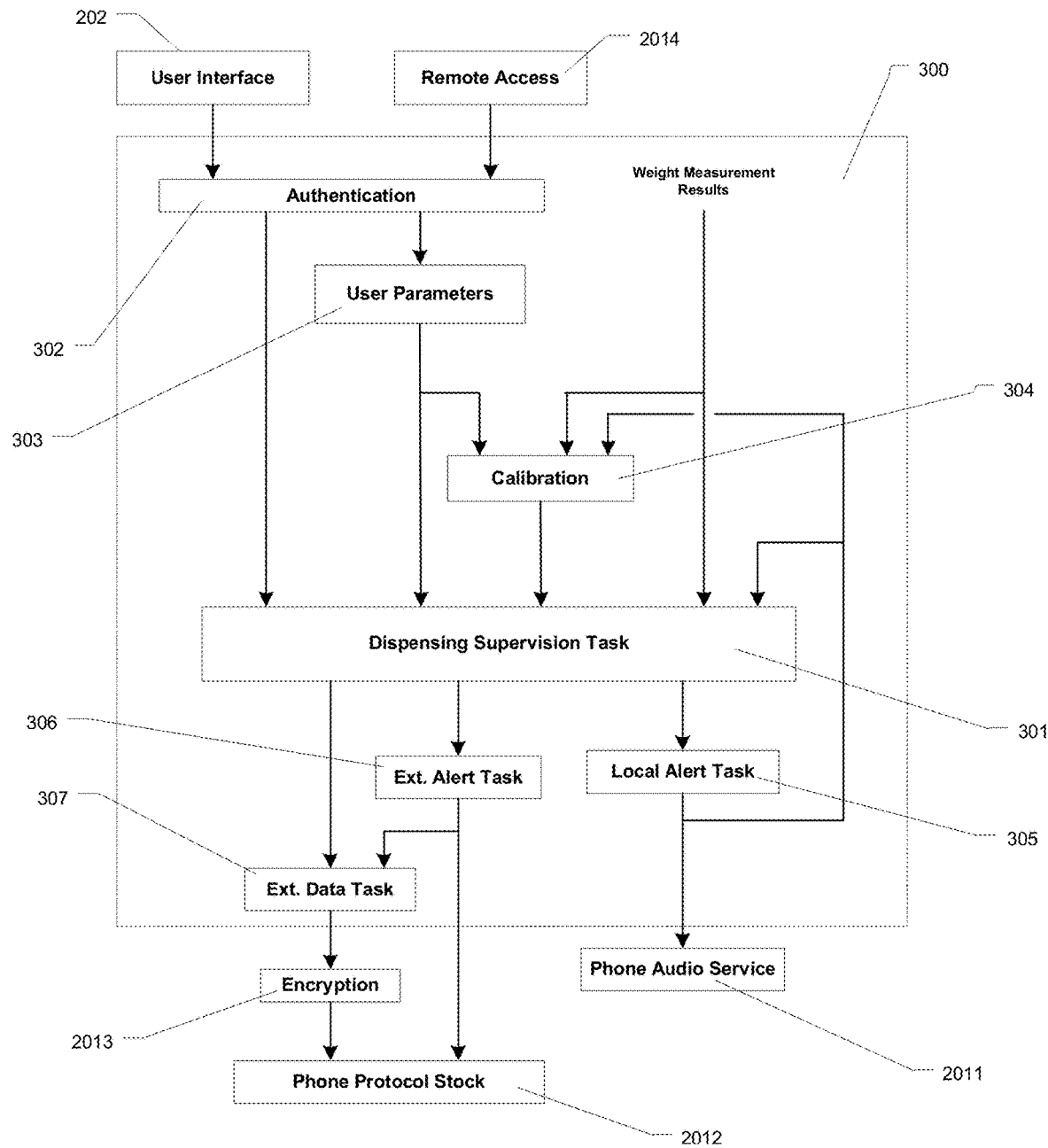
FIG. 3 is a flowchart of an exemplary method for processing of the cell-phone based medicine dispensing application.

The functional relationship of various operational parameters necessary to control dispensing application is presented in FIG. 3. Operational parameters, current dispense status (medication status after last dispense period), and the current measurements obtained from the dispense unit are presented to the Dispense Supervision Task 301.

Operational parameters, such as: user parameters 303 consisting among others: order and phone numbers, medication name dosage and dispense schedule, medication related instructions, pharmacy and provider instructions and messages; medication calibration parameters 304; local alert messages 305; and external alert messages 306. Operational parameters are entered by the pharmacy personnel into medication schedule form, then data from said schedule form is after formatted, encapsulated and used to generate a 2D bar-code which is then scanned into the medication dispensing application using UI 202. Such entry of the schedule may be performed at the pharmacy or by the healthcare provider or medical supervisor. Furthermore, some of the parameters, such as changes in amount of medication to be taken, can be modified remotely by an authenticated medical supervisor using the WAN/PAN radio interface 2014.

Figure 4:
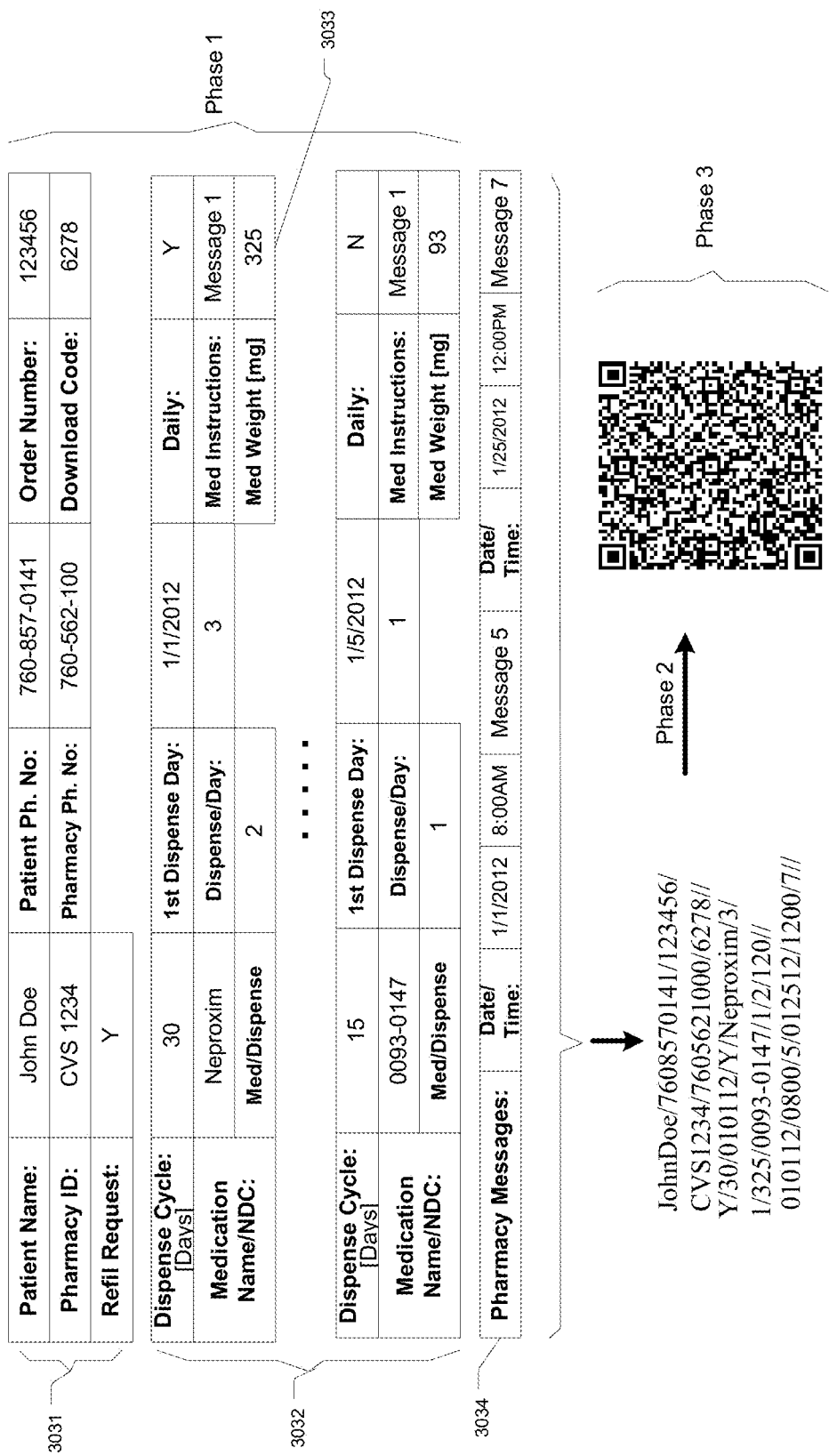
FIG. 4 is an exemplary flow of entering patient medication schedule.

An exemplary procedure of schedule preparation and entry consists of three steps/phases is presented in FIG. 4.

In phase 1, the pharmacy or the caregiver fills the user parameters 3031, medication parameters 3032 and 3033, and the message parameters 3034, into the medication schedule form.

In phase 2, data from the medication data entry the schedule from is extracted, processed to remove redundancies and formatted. Then formatted data is used to generate the 2D bar-code, such as QR code.

In phase 3, the QR code is scanned into the application using mobile terminal UI, data is extracted and inserted into application DB. Said entry (scanning) of the 2D bar-code may be performed at the pharmacy or even by the user after such selected user provides a valid download code associated with the medication order number.

Figure 5:
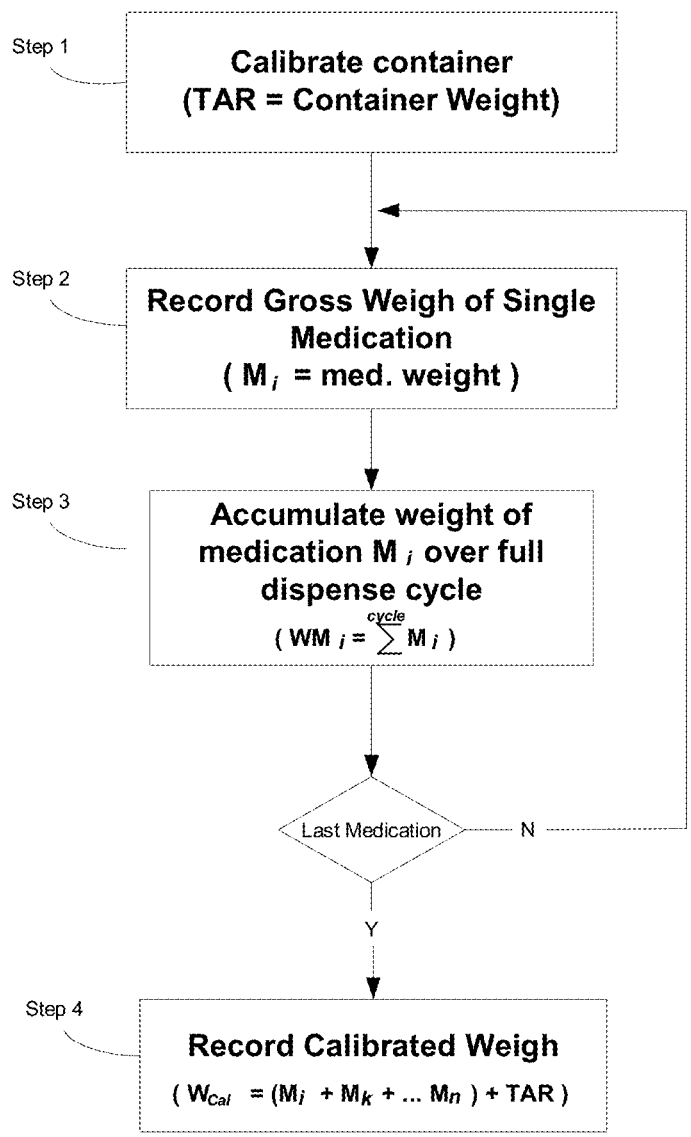
FIG. 5 is an exemplary flowchart of initial calibration procedure.

Operational parameters entered through the process described in FIG. 4, together with medication calibration data obtained in process described in FIG. 5, and with the measurements obtained from the dispense unit during the dispense process are used to provide verification of compliance with the medication schedule. An exemplary procedure of verification of compliance is presented in FIGS. 6 and 7.

Furthermore, medication specific messages 3034 may contain instructions intended for the selected user requesting pre/post dispense monitoring of physiological functions effected by the prescribed medication. Such monitoring instruction may contain request to connect a specific monitor, such as Blood Pressure monitor 400, or Glucose Level monitor 500 presented in FIG. 8, to allow verification of effects of medication on the selected user. A range of acceptable variation of the monitored physiological functions before triggering an automatic notification of medical personnel of medical supervisor. The results of said monitoring may stored in the medication dispense application memory for further analysis or if the monitored function exceeds predefined threshold, may be transmitted to the medical supervisor.

Referring back to schedule form and medication entry method presented in FIG. 4. Here we see the first information 3031, includes identity information of the user, pharmacy, medical personnel and a plurality of parameters indicating phone numbers or IP addresses of family members, medical personnel, etc.

The second information 3032, includes medication information and a plurality of parameters defining medication dispense cycle, such as: start and end of the cycle; number of dispenses per day; daily dispense schedule; etc.

The third information, 3033, includes plurality of parameters, such as: medication name in form of NDC (National Drug Code) code registry; number of each individual medications to be dispensed in each dispense period; calibrated gross weigh of each medication; medication specific instructions, such as: instruction to take medication after food; requests to monitor specific bio-functions—for example: heart rate, blood pressure, etc. as well as interval at which such function shall be performed (before or after medication dispense); etc.

The forth information, 3034, includes special instructions and more specifically plurality of parameters such as: pharmacy specific messages—for example: medication refill info, instruction on medication safety, links to instructional materials, links to references on interactions with different types of medications, discounts, etc; provider messages—for example: schedule of next office visit, request to provide feedback on medication effectiveness, instruction to monitor physiological functions which may be effected by the prescribed medication, thresholds to trigger automatic notifications if the monitored physiological function exceeds predetermined safety limit, etc; caregiver messages—for example: request for permission to retrieve the medication adherence log; etc.

Figure 6:
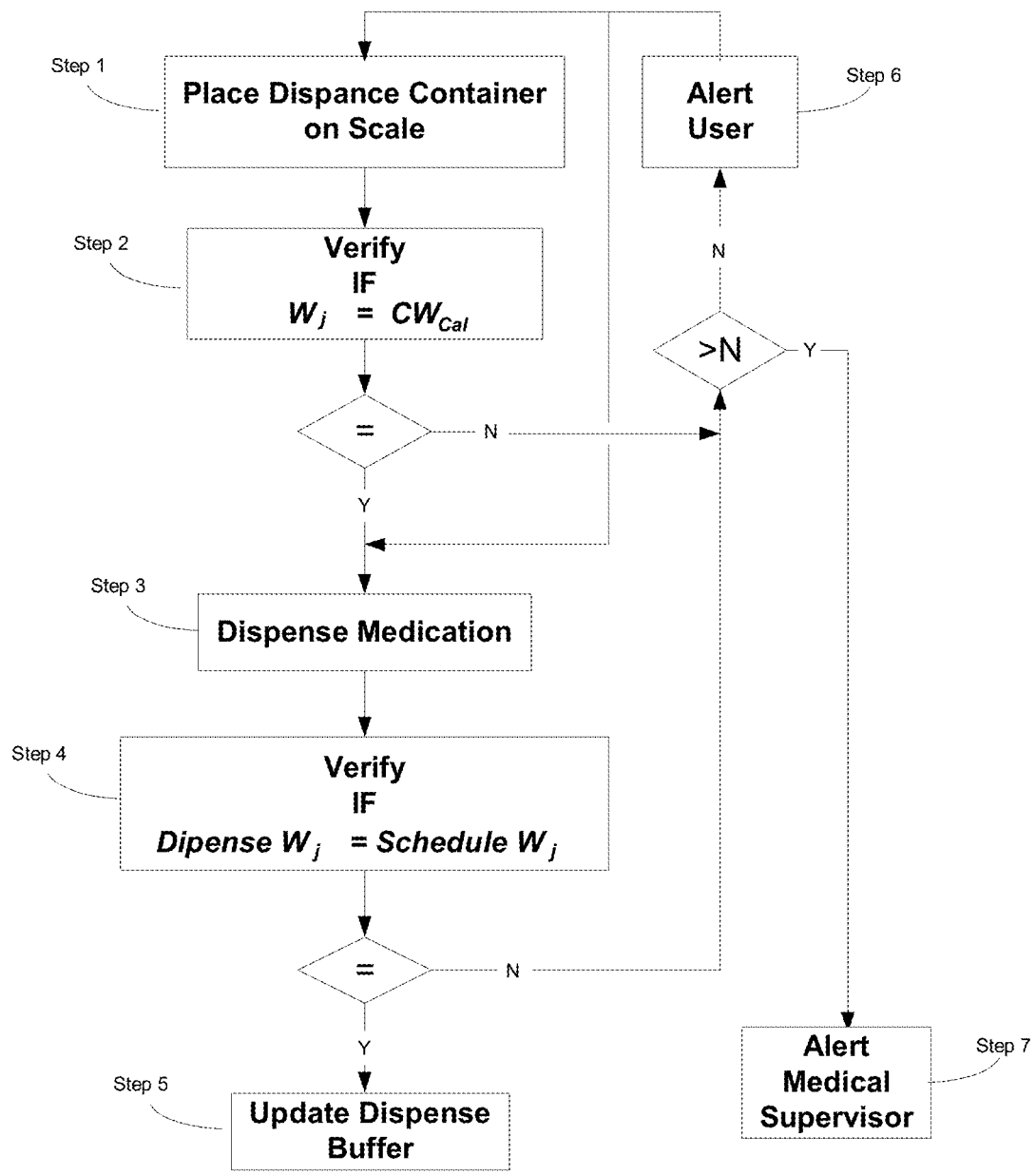
FIG. 6 is an exemplary flowchart of current (pre/post dispense) calibration procedure.

The fifth information, 3035 of FIG. 6, which is stored in Approved Response Buffer, includes a list of valid responses pre-approved by the medical supervisor used to cancel local alerts, such as: response to allow deviation form dispense schedule—for example "Medication taken ahead of time due to specific medical condition", etc. Such valid responses may be selected from the list included into the pharmacy instruction messages embedded into the medication schedule.

Figure 7:
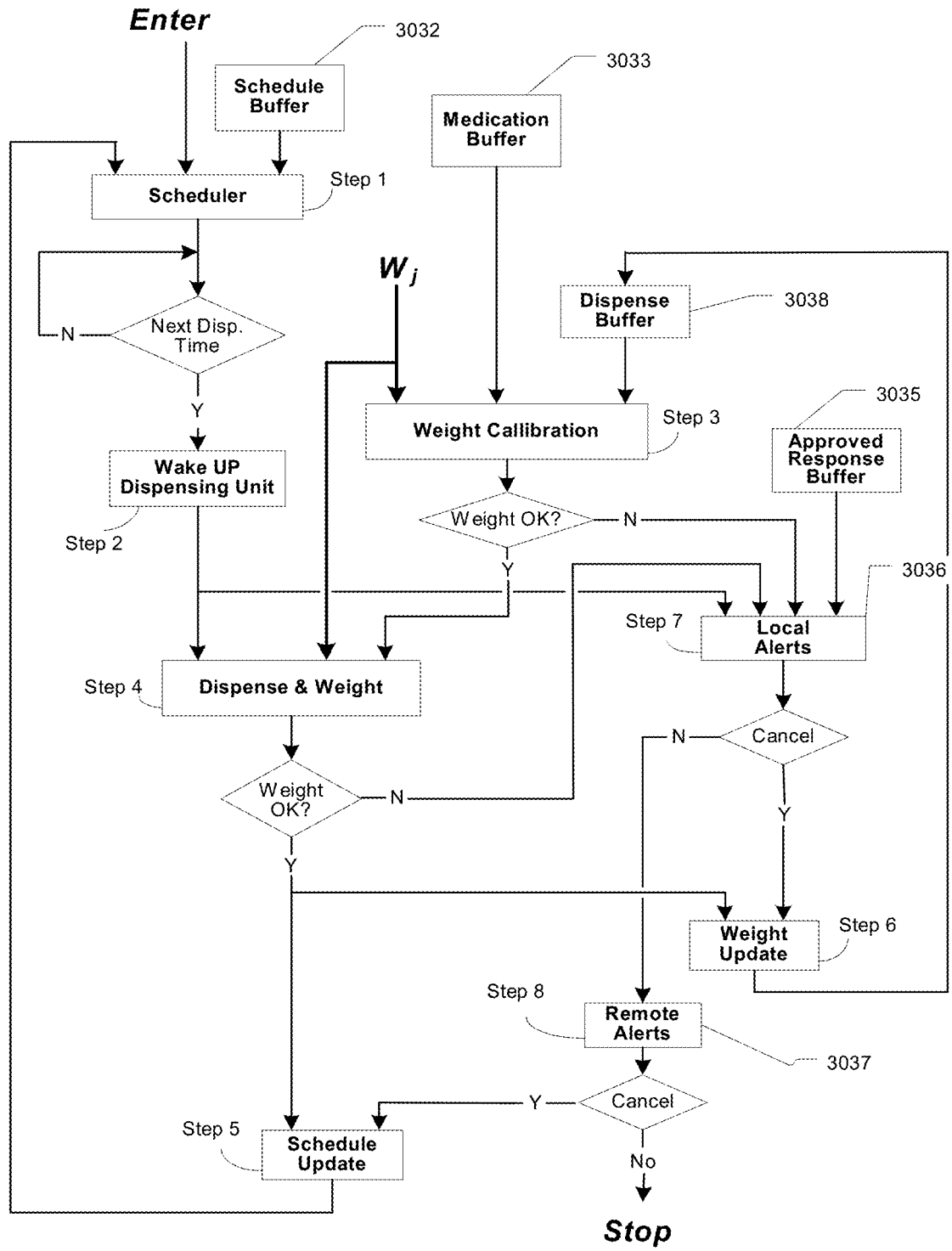
FIG. 7 is a flowchart of an exemplary method of the supervisory process of the exemplary medicine dispensing application.

The sixth information, 3036 of FIG. 7, stored in the Local Alerts Buffer, contains local alert messages and the actions the monitoring application must take in various cases. More specifically, it may contain the selection of one or more of the predefined audio and/or textual messages intended to alert the user/patient about the next medication dispense time or in case such dispense didn't occurred or if the dispensed amount was different from the scheduled one or in the case the total medication weight before dispense was not equal to the weight stored after the previous dispense.

The seventh information, 3037 of FIG. 7, stored in the Remote Alerts Buffer, contains the type of remote alerts messages and the actions the monitoring application must take in such cases. More specifically, it may contain the selection of one or more of the predefined audio and/or textual messages intended to alert the patient medical supervisor about the discrepancy in medication dispensing or in case medication dispensing didn't occur, or if the dispensing amount was different from the scheduled one or in the case the total medication weight before dispensing was not equal to the weight stored after the previous dispensing and the local alert was not canceled by the user/patient corrective action.

The eight information, 3038 of FIG. 7, stored in the Dispense Buffer, contains plurality of weight parameters such as: the calibrated gross weight of each individual medication; a combined gross weight of each type of medication for the entire dispense cycle; a combined gross weight of each medication for a single dispense period; a combined gross weight of all medication for each dispense period; a calibrated weight of medications, including the gross weigh of all scheduled for the entire dispense cycle plus the tar weigh of the medication container; a post-dispense combined weight of each type of medication; a post-dispense combined weight of all medications; and a weight of the empty dispense container. The INITIAL calibrated values of those parameters are obtained during the initial calibration process, while the CURRENT calibrated values of those parameters are obtained after dispensing by subtracting recently dispensed values from the previously stored values.

The INITIAL_CALIBRATION process is performed by the pharmacy personnel or by health provider personnel or by an authenticated medical supervisor. The data entered in the schedule form is processed to produce a 2D bar-code, then entered into the application via terminal UI, by scanning of said 2D bar-code. The above procedure consist of four steps and is presented in FIG. 5.

In Step 1, the application sends a request to device UI to activate the dispenser and place the empty dispense container on the scale. After obtaining reliable measurement (for example by averaging several independent measurements to reduce variance of such measurement to acceptable accuracy), the weight of an empty container is stored as a Tar Weight.

In Step 2, the medicine dispensing application sends a request to the device UI to place a single Medication_Name$_{(i)}$ ($M_i$) into the container then record the changes in the weight (Tar_Weight+medication) as a Gross_Weight ($WM_i$) of medication I, where then medication gross weight is the combined weight of medication active ingredient (usually listed on medication container or associated with medication NDC), plus the weight of all bonding and coating compounds. As such, the Gross_Weight, of 2 mg dosage of Nitroglycerine will actually record 26 mg. Alternatively, if the GROSS_WEIGHT is known, for example, by the pharmacy staff, etc. such amount may be entered directly into the schedule medication record.

In Step 3, the application calculates the Total_Weight of medication i to be dispensed during the dispense period, this is performed by accumulation of the weight of single medication*the number of dispense period (day)*the number of days in the dispense cycle, such as:

$$WM_i = M_i * \text{Medication/Dispense} * \text{Days/Cycle}$$

Application returns to Step 2 until last medication is calibrated.

In Step 4, the application accumulates the Total_Weight of all medications then adds the Tar_Weight and store such value as a Initial_Calibrated_Weight:

$$(IW_{Cal} = (M_i + M_k + \ldots + M_n) + TAR$$

After each dispense period, application subtracts the currently dispense weight for each medication form $WM_i$ then saves the new Total_Weight, as the Current_Total_Weight ($WCM_i$) of medication i. This is done for each dispensed medication and after Current_Total_Weight for all medication is updated, a Current_Calibrated_Weight ($CW_{Cal}$) is recorded.

At each dispense period, and before any medication is dispensed, application executes CURRENT_CALIBRATION. This seven steps process is performed automatically before each dispensed period and is presented in FIG. 6.

In Step 1, the application sends a message the device UI requesting placement of the medication container with medications on the scale.

In Step 2, after obtaining reliable measurement from the scale (for example by averaging multiple independent measurements to reduce variance of such measurement to acceptable accuracy), the application, verifies if the measurement ($W_j$) equals the Current Calibrated_Weight ($CW_{Cal}$), If the measurement ($W_j$) equals the Current Calibrated_Weight ($CW_{Cal}$), application proceeds to Step 3 and instructs through the device UI to take medication. If the measurement ($W_j$) does not equals the Current Calibrated_Weight ($CW_{Cal}$), and the number of corrective requests is less then specified in Operational Parameters, application proceeds to Step 6 alerting user through the device UI to correct medication error or select one of the pre-approved reasons for deviation between the measured weigh ($W_j$) and the Current Calibrated_Weight ($CW_{Cal}$). Otherwise, if the number of corrective requests exceeds the number predefined in the Operational Parameters, application proceeds to Step 7 and alerts remote medical supervisor of medication non-compliance.

After medication is dispensed in Step 3, application enters Step 4 and verifies if the Dispensed_Weight ($DW_j$) equals the Scheduled_Weight ($SW_j$). If the Dispensed_Weight ($DW_j$) equals the Scheduled_Weight ($SW_j$), application enters Step 5 and updates the Current Calibrated_Weight ($CW_{Cal}$), and the Current_Total_Weight ($WCM_i$) of each medication remaining in the dispenser. If the Dispensed_Weight does not equals the Scheduled_Weight ($SW_j$), and the number of corrective requests is less then specified in Operational Parameters, application enters to Step 6, then after alerting user, enters Step 3 and waits for corrective action. If the number of corrective requests is more then specified in Operational Parameters, application enters Step 7 and alerts remote medical supervisor of medication non-compliance.

The information contained within the Operational Parameters is used by the Dispensing Supervision task 301 of FIG. 3. The operation of the Dispense Supervision task is presented in FIG. 7 and described below.

In Step 1 of FIG. 7 after the ENTER, the Scheduler programs all appropriate timers with the values defined by the second information 3032, then start the application, and when the next dispense interval arrives, application enters Step 2.

In Step 2, application wakes-up the dispensing unit by sending appropriate commands over wireless interface, then enters Steps 4, and waits for conformation by the user of incoming medication period (Step 7), and for the results of the CURRENT_CALIBRATION procedures (Step 3).

In Step 3, application, by comparing the current weight measurement ($W_j$) with the Current Calibrated_Weight ($CW_{Cal}$), verifies correct amount of medication in the dispense container. If weight ($W_j$) equals the Current Calibrated_Weight ($CW_{Cal}$), application proceeds to Step 4. If weight ($W_j$) is not equals the Current Calibrated_Weight ($CW_{Cal}$), application proceeds to Step 7.

In Step 4, application retrieves medication parameters stored in s 3033, retrieves the number of medications and the Gross_Weight ($WM_i$) of each medication, then, through the device UI instructs the user to remove medication prescribed for this dispense period. After medication is dispensed, it subtracts Scheduled_Weight ($SW_j$), from the Current_Calibrated_Weight ($CW_{Cal}$). If the result equals measured weight ($W_j$), application proceeds to Step 5 to update the schedule time and to Step 6 to update the Current_Calibrated_Weight($CW_{Cal}$) value in the Dispense Buffer 3038. If the result does not equal measured weight ($W_j$), application proceeds to Step 7.

In Step 7, application waits until local alert is canceled or until the time stored in Operational Parameters elapses. Local alarms may be in the form of predefined audio or textual messages.

In response to local alarm, user may select on entries from the list of valid reasons, which are pre-approved by the medical supervisor and stored in Approved Reasons Buffer 3035. One entry in such list may be for example be: needs to take medication ahead of time due to health condition; another, the user schedule conflict; yet another, a recent directive by the medical personnel. If a valid reason for such discrepancy was received, a new weight value for the Current_Calibrated_Weight($CW_{Cal}$) is calculated in Step 6, and stored in the Dispense Buffer 3038, and the dispensing process may continue to Step 4.

Local alerts and the pre-approved responses for temporary deviations in the amount (weight) of medication to be dispensed, allows for emergency dispensing as well as recovery from minor patient or system errors, such as: out of RF coverage area; battery power down, etc. while still providing high reliability and minimizing unnecessary external alarms.

If the local alert is not cancelled within the period of time defined in Operational Parameters, the application proceeds to Step 8.

In Step 8, application sends an external alert to the predefined recipients over the cellular network then waits for the medical supervisor corrective action. Such corrective action may be in the form of acceptance to non-compliance, changes to the user medication schedule, etc. The corrective action in response to external alerts may be performed after proper authentication, either locally by logging into the application using phone UI 202, or remotely using API interface. If such intervention is not received within the time period specified in Operational Parameters, the application goes to the STOP state, from which it can only recover after RESET provided of by the medical supervisor.

Depending on the type of the dispensing container design, the dispensing application may instruct the container to open the "current" compartment, or wait for an ACCEPT command from a dedicated unit interface (i.e. push-button), or simply monitor the change in the weight of the dispensing container.

Figure 8:
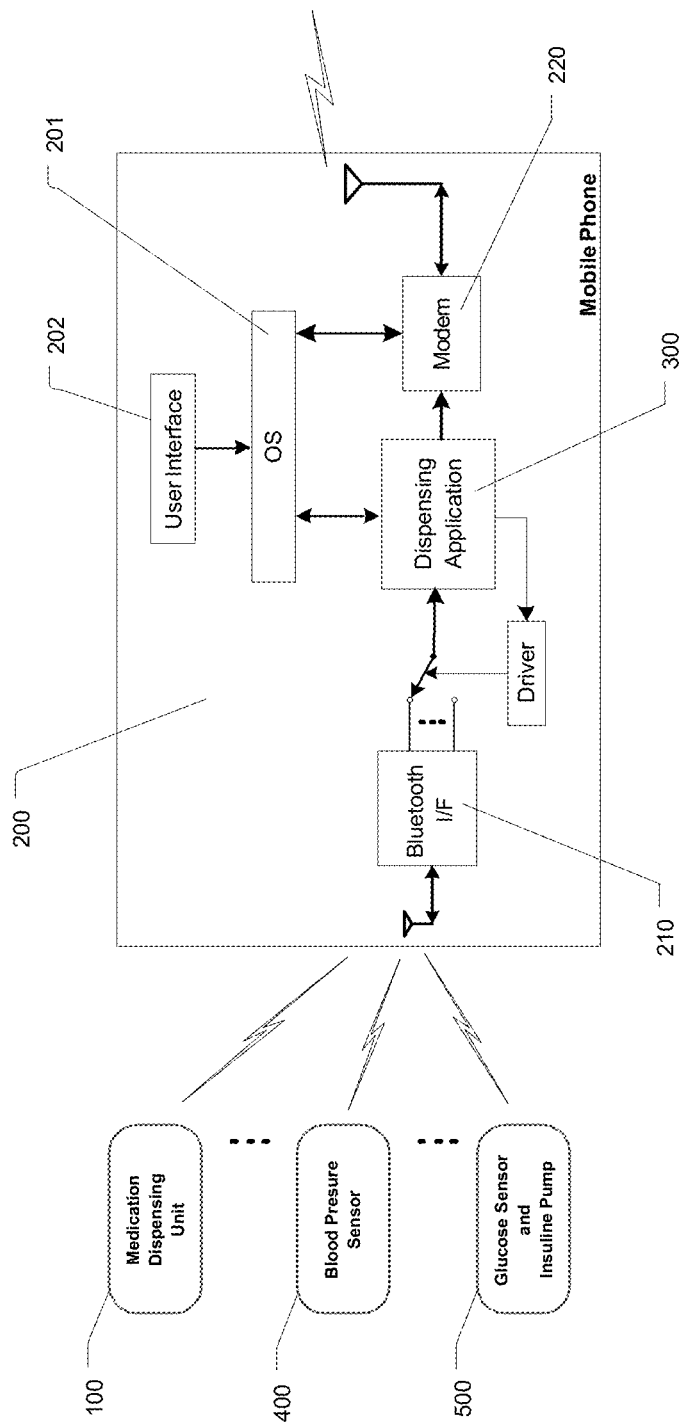
FIG. 8 is a block diagram of the medicine dispensing and analysis system.

In the embodiment of FIG. 8, the application 300 includes additional functionality supporting pre/post dispense monitoring of various physiological functions, such as: blood pressure sensor 400; glucose level sensor 500, heart rate/arrhythmia sensor, etc. Such functionality can provide real-time feedback to the medical personnel regarding patient's reaction to medication.

In such embodiment, at the predefined time, or before and/or after medication dispensing, application alerts user, then instructs to connect a particular monitoring device and/or inform about procedure related to monitor a specific physiological function. The results of such monitoring may be stored in the medicine dispensing application for later retrieval or may be send directly to the medical supervisor if said measurement exceeds thresholds defined in information 3034.

If the measurement results are to be sent to the external destination, the application's External Data Task 307 (FIG. 3), formats the data records, then using encryption service 2013 sends data to the cellular modem for transmission over the WAN wireless network.

We claim:

1. A medicine dispensing system comprising:
   a medicine dispensing unit comprising a weighting unit and a medicine container comprising individual compartments associated and corresponding to a single day dosage of medication; and
   a medicine dispensing application in wireless communication with the medicine dispensing unit and with a selected user,
   wherein the medicine dispensing application is configured to obtain a plurality of medication parameters from a QR (Quick Response) code, and wherein the medication dispensing application is further configured to obtain a calibrated weight of medication.

2. The medicine dispensing system of claim 1, wherein the plurality of medication parameters included in a QR (Quick Response) code comprise:
   selected user information;
   a calibrated weight of medication scheduled for dispense;
   medical instructions pertaining to scheduled medication;
   messages and instructions from a pharmacy and a health care provider; and
   wherein the medical instructions pertaining to the scheduled medication comprise a cross-references of interactions between different medications and links to instructional materials, wherein the messages and instruction from the pharmacy comprises promotional materials and discount coupons, and wherein the medical instructions from the health care provider comprise instructions to perform pre-dispense and/or post-dispense monitoring of selected physiological parameters influenced by medication and to schedule office visit and to provide feedback on reactions to dispensed medication.

3. The medicine dispensing system of claim 2, wherein the messages and instructions from the pharmacy and the messages and instructions from the health care provider are referenced by an identifier pertaining to the preceded information stored in a medicine dispensing application memory.

4. The medicine dispensing system of claim 2, wherein the medicine dispensing application is configured to extract from a QR (Quick Response) code: medication schedule, calibrated weight of medication, medical instructions and messages and instructions from pharmacy and health care provider; and use the medication schedule, calibrated weight of medication, medical instructions and messages and instructions from pharmacy and health care provider to instruct the selected user of an incoming medication dispense period by means of pre-encoded audio or textual messages stored in the medicine dispensing application.

5. The medicine dispensing system of claim 2, wherein maintaining of a calibrated weight of medication comprises:
   retrieving the calibrated weight of medication stored after previous dispense period and verifying the calibrated weight medication equal to weight of medication stored in a medication container;
   retrieving a calibrated weight of medication scheduled for a current dispense period;
   verifying the calibrated weight of medication dispensed equals to the calibrated weight of medication scheduled for the current dispense period;
   subtracting the calibrated weight of medication dispensed during the current dispense period from the calibrated weight of medication; and
   storing result as the calibrated weight of medication.

6. The medicine dispensing system of claim 2, wherein obtaining a calibrated weight of medication scheduled for dispense comprises:
   obtaining a weight of an empty medicine container;
   obtaining a calibrated weight of medication for dispense during a dispense period by accumulating gross weight of all medication scheduled for the dispense period;
   obtaining a calibrated weight of medication scheduled for dispense during a dispense cycle by multiplying the calibrated weight of the single medication by number of medications scheduled for dispense during the dispense cycle, then adding the calibrated weight of medication to the weight of the empty medicine container; and maintaining the calibrated weight of medication.

7. A medicine dispensing system comprising:
a wireless port for providing bi-directional communication with a dispensing unit and another wireless port providing bi-directional communication with a cellular network;
a processor coupled to the wireless ports;
a non-transitory memory medium coupled to the processor, wherein the non-transitory memory medium comprises program instructions executing all of the following:
 extracting:
  selected user information;
  a calibrated weight of medication scheduled for dispense;
  medical instructions pertaining to a medication scheduled for dispense;
  messages and instructions from a pharmacy and messages and instructions from a health care provider from a selected user medication schedule;
 performing encapsulation and compression of information records containing:
  the selected user information;
  the calibrated weight of medication scheduled for dispense;
  the medical instructions pertaining to the medication scheduled for dispense; and
  the messages and instructions from a pharmacy and the messages and instructions from a health care provider, into a QR (Quick Response) code;
 disassembling the QR code into individual parameters used to control functionality of the medicine dispense system;
 obtaining a calibrated weight of medication by:
  obtaining a weight of an empty medicine container;
  obtaining a calibrated weight of a single medication by measuring a single medication gross weight;
  obtaining a calibrated weight of medication for dispense during a dispense period by accumulating a gross weight of all medication scheduled for said dispense period;
  obtaining a calibrated weight of medication scheduled for dispense during a dispense cycle by multiplying the calibrated weight of the single medication by number of medications scheduled for dispense during the dispense cycle; and
  adding the calibrated weight of medication to the weight of the empty medicine container; and
 maintaining the calibrated weight of medication during the dispense period.

\* \* \* \* \*